(12) United States Patent
D'Andrea

(10) Patent No.: US 9,192,345 B2
(45) Date of Patent: Nov. 24, 2015

(54) RADIATION DEVICES AND METHODS

(71) Applicant: Mark A. D'Andrea, Houston, TX (US)

(72) Inventor: Mark A. D'Andrea, Houston, TX (US)

(*) Notice: Subject to any disclaimer, the term of this patent is extended or adjusted under 35 U.S.C. 154(b) by 185 days.

(21) Appl. No.: 13/793,184

(22) Filed: Mar. 11, 2013

(65) Prior Publication Data

US 2014/0257088 A1    Sep. 11, 2014

(51) Int. Cl.
| | |
|---|---|
| *A61B 6/12* | (2006.01) |
| *A61B 6/00* | (2006.01) |
| *A61N 5/10* | (2006.01) |
| *A61F 7/12* | (2006.01) |
| *A61B 5/00* | (2006.01) |
| *A61M 25/01* | (2006.01) |

(52) U.S. Cl.
CPC ............ *A61B 6/425* (2013.01); *A61B 5/6853* (2013.01); *A61F 7/123* (2013.01); *A61N 5/1048* (2013.01); *A61B 5/4836* (2013.01); *A61B 5/4839* (2013.01); *A61M 25/0108* (2013.01); *A61N 5/1014* (2013.01)

(58) Field of Classification Search
CPC .... A61B 6/425; A61B 5/6858; A61B 5/6859; A61B 5/6852; A61B 5/6853; A61B 5/4836; A61B 5/4839; A61F 7/123; G01T 1/161; A61M 25/0108; A61N 5/1014; A61N 5/1048
USPC ......................................... 600/424, 435, 436
See application file for complete search history.

(56) References Cited

U.S. PATENT DOCUMENTS

| | | |
|---|---|---|
| 899,477 A | 9/1908 | Williams |
| 3,060,924 A | 10/1962 | Rush |
| 3,173,418 A | 3/1965 | Baran |
| 3,435,826 A | 4/1969 | Fogarty |
| 3,467,101 A | 9/1969 | Fogarty et al. |
| 3,543,744 A | 12/1970 | LePar |
| 3,841,304 A | 10/1974 | Jones |
| 3,861,380 A | 1/1975 | Chassagne et al. |
| 4,263,917 A | 4/1981 | Moss |
| 4,294,264 A | 10/1981 | Fischell et al. |

(Continued)

FOREIGN PATENT DOCUMENTS

| | | |
|---|---|---|
| CA | 699316 | 12/1964 |
| GB | 1511557 | 5/1978 |

OTHER PUBLICATIONS

Price et al., "Development of a RadFET Linear Array for Intracavitary in vivo Dosimetry During External Beam Radiotherapy and Brachytherapy", Aug. 2004, IEEE Transactions on Nuclear Science, vol. 51, No. 4, p. 1420-1426.*

(Continued)

*Primary Examiner* — Long V Le
*Assistant Examiner* — Angela M Hoffa
(74) *Attorney, Agent, or Firm* — Cook Alex Ltd.

(57) ABSTRACT

Radiation diagnosis devices, systems and methods are in general catheter form and include at least one diagnostic balloon that provides at least one diagnosis function and assists in placement of at least one radiation detector at a desired diagnosis location within an existing body cavity or at a percutaneous site. Data collected by the detector that is positioned as determined by the medical professional allows the medical professional to monitor radiation levels, either residual from a prior radiation treatment, during a brachytherapy treatment at the diagnostic catheter insertion site or in adjoining site, or during externally administered radiation.

16 Claims, 2 Drawing Sheets

(56) References Cited

U.S. PATENT DOCUMENTS

| | | | |
|---|---|---|---|
| 4,318,410 | A | 3/1982 | Chin |
| 4,323,055 | A | 4/1982 | Kubiatowicz |
| 4,349,033 | A | 9/1982 | Eden |
| 4,434,789 | A | 3/1984 | Kumar |
| 4,471,779 | A | 9/1984 | Antoshkiw et al. |
| 4,631,415 | A | 12/1986 | Sauerwein et al. |
| 4,733,653 | A | 3/1988 | Leung et al. |
| 4,744,366 | A | 5/1988 | Jang |
| 4,775,362 | A | 10/1988 | Kronner |
| 4,813,934 | A | 3/1989 | Engelson et al. |
| 4,861,520 | A | 8/1989 | van't Hooft et al. |
| 4,881,937 | A | 11/1989 | van't Hooft et al. |
| 4,881,938 | A | 11/1989 | van't Hooft et al. |
| 4,897,076 | A | 1/1990 | Puthawala et al. |
| 4,919,651 | A | 4/1990 | Doane |
| 4,969,863 | A | 11/1990 | van't Hooft et al. |
| 5,012,357 | A | 4/1991 | Schoeppel et al. |
| 5,019,042 | A | 5/1991 | Sahota |
| 5,049,132 | A | 9/1991 | Schaffer et al. |
| 5,090,043 | A | 2/1992 | Parker et al. |
| 5,106,360 | A | 4/1992 | Ishiwara et al. |
| 5,122,113 | A | 6/1992 | Hattler |
| 5,135,494 | A | 8/1992 | Engelson et al. |
| 5,147,300 | A | 9/1992 | Robinson et al. |
| 5,306,271 | A | 4/1994 | Zinreich et al. |
| 5,342,305 | A | 8/1994 | Shonk |
| 5,520,646 | A | 5/1996 | D'Andrea |
| 5,653,683 | A | 8/1997 | D'Andrea |
| 5,720,717 | A | 2/1998 | D'Andrea |
| 5,913,813 | A | 6/1999 | Williams et al. |
| 6,312,375 | B1 | 11/2001 | Montebello et al. |
| 6,413,204 | B1 | 7/2002 | Winkler et al. |
| 6,482,142 | B1 | 11/2002 | Winkler et al. |
| 6,699,171 | B2 | 3/2004 | Harmon |
| 7,534,202 | B2 | 5/2009 | Eng |
| 7,556,596 | B2 | 7/2009 | Mourtada et al. |
| 7,651,458 | B2 | 1/2010 | Mourtada et al. |
| 7,666,130 | B2 | 2/2010 | Mick |
| 8,033,979 | B2 | 10/2011 | Mick |
| 8,500,771 | B2 * | 8/2013 | Isham ............................ 606/197 |
| 8,636,637 | B2 * | 1/2014 | Lubock et al. .................... 600/3 |
| 2002/0111560 | A1 * | 8/2002 | Kokate et al. .................. 600/549 |
| 2003/0153803 | A1 | 8/2003 | Harmon |
| 2004/0147811 | A1 * | 7/2004 | Diederich et al. ............ 600/207 |
| 2006/0116546 | A1 | 6/2006 | Eng |
| 2010/0145132 | A1 | 6/2010 | Isham |

OTHER PUBLICATIONS

Horton, John et al., LDR Intracavitary Brachytherapy Applicators, UT MD Anderson Cancer Center Intracavitary Brachytherapy, 2005.
http://www.cancer.org/Treatment/TreatmentsandSideEffects/TreatmentTypes/hyperthermia, Downloaded May 2, 2012.
Research Spotlight, Eos, vol. 92, No. 33, Aug. 16, 2011.
Zhu, Timothy C., Diode Dosimetry for Megavoltage Electron and Photon Beams, Dept. of Radiation Oncology, U. of Pennsylvania, Philadelphia, PA, Jun. 24, 2009.
Dutta, Pinaki, MD et al., How is radiation therapy given?, OncoLink Cancer Resources, www.oncolink.org/treatment/article, Downloaded Oct. 28, 2011.
http://vantageoncology.com/centers2006/html/body/treatment/wildomar, High-Dose Rate Brachytherapy (HDR)TandemandOvoid Implant, WildomarRadiationTherapyCentr, Download Oct. 31, 2001.
www.americanbrachytherapy.org/aboutBrachytherapy,What is Brachytherapy?, American Brachytherapy Society, Downloaded Nov. 4, 209.
Section III: Disease Sites, Chapter 22: Uterine Cervix, textbook pp. 657-659, circa 2001.
Corrao, Anita, MS, CMA, Dabre, A comparison of APBI brachytherapy techniques: MammoSite . . . , Lifespan, Providence, RI, 2010.
MicroSelectron—body site applicator solutions, Oncoselect by Nucletron, circa Mar. 2010.

\* cited by examiner

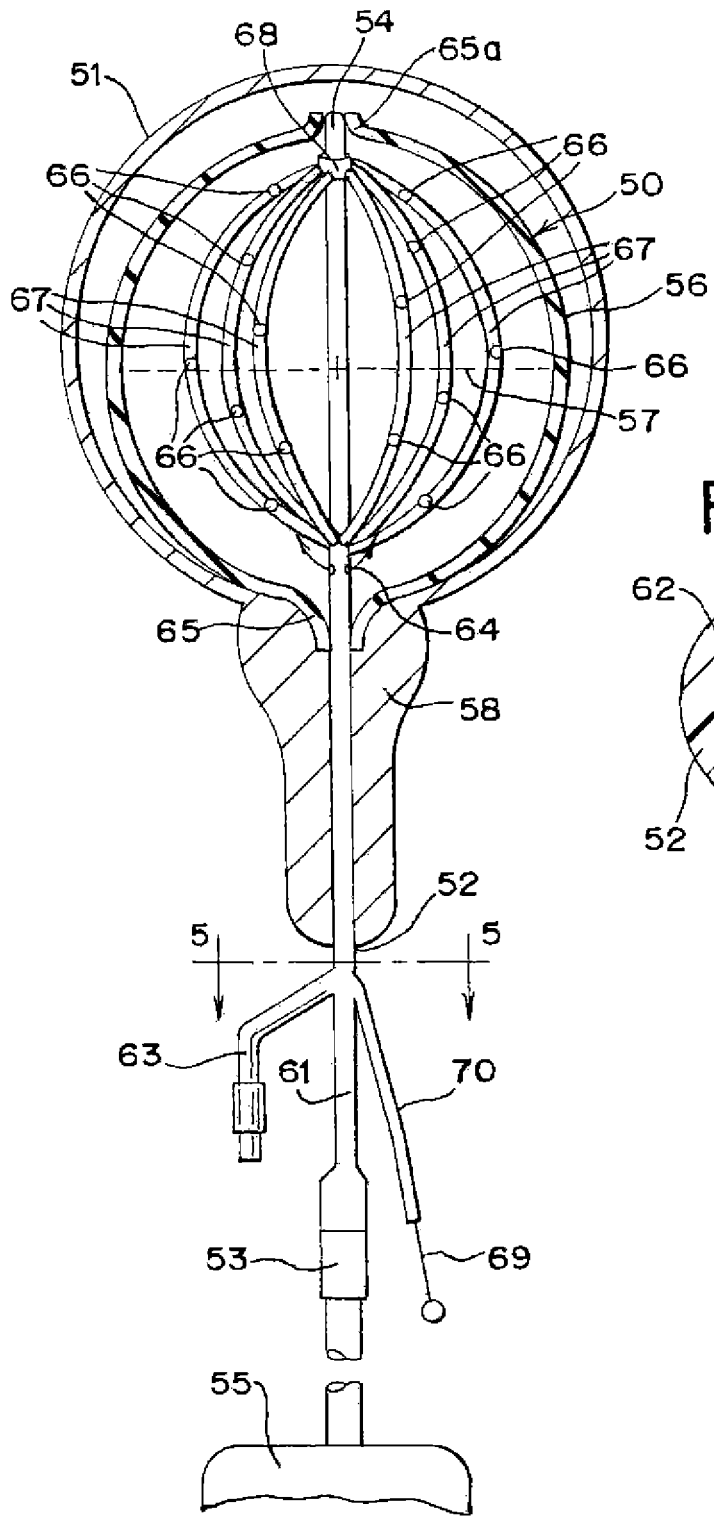
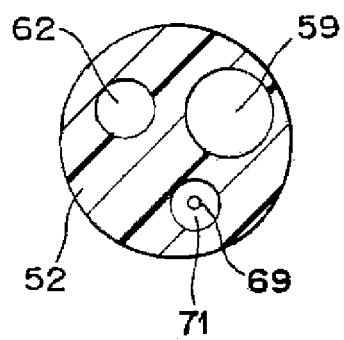
FIG.4
FIG.5

RADIATION DEVICES AND METHODS

TECHNICAL FIELD

The present subject matter relates to devices, systems and procedures used during radiation diagnosis. When retained in place during treatment, the subject matter encompasses in-place marking and tracking of radiation treatment patterns and effectiveness. The overall technical field involves radiation oncology procedures with respect to a wide variety of cancerous conditions. Diagnosis, marking, mapping and evaluation are carried out by implements incorporating balloon technology in combination with other technologies which together enhance the precision and accuracy of cancer treatment diagnosis, mapping, marking and tracking before, during and after radiation treatment.

BACKGROUND

Diagnostic and marking systems, devices and methods are known and used by medical professionals in dedicated units of numerous hospitals and free-standing cancer treatment centers, and some incorporate balloons to achieve and maintain proper placement during diagnosis.

Diagnostic and marking tasks often utilize devices of the type intended to be inserted into living body cavities through existing body orifices or into surgically executed openings for treatment under the skin of a patient. For example, once a catheter and its balloon are inserted in a prescribed manner into a body cavity, its balloon can be inflated to mark the boundary of the body cavity during radiographic examination, and the inflated balloon may also be used to move, push or otherwise manipulate body tissue during the diagnostic procedure.

Various devices, systems and methods have been developed, each typically being designed for a specific diseased body organ, area or part and/or for one or more treatment locations. Whether a treatment regimen involves a one-step or a multi-step protocol, it is important to maintain a good balance among radiation dosage, placement and timing. To do so requires precision in diagnosis so that the target location or locations are treated with the radiation source while protecting as much as possible areas of the body that are disease-free and otherwise could be vulnerable to unintended treatment if positioning with respect to the treatment locations is not modified during diagnosis, marking and treatment.

Proper, precise and accurate marking, diagnosis and manipulation procedures can precede and be reproduced or maintained during carcinoma treatment procedures, such as when following high dose rate (HDR) brachytherapy. At times, the diagnoses by the radiation oncologist will be intended for regimens using low dose rate (LDR) brachytherapy, typically based on cesium delivery as in $^{137}$Cs. For HDR brachytherapy regimens, $^{192}$Ir is frequently used because of its high specific activity. Diagnoses for using other isotopes are available and used as warranted. The degree of treatment measurement is in terms of units of radiation exposure (in roentgens or Gray or Gy), and often these are prescribed at specific locations and points. Details in this regard are known to radiation oncologists, medical physicists and other medical professionals experienced in brachytherapy and cancer treatment in general. An objective also is to provide reasonably constant and predictable dose rates at each specific location that diagnosis and marking have determined are most beneficial for the patient.

Intracavitary and percutaneous radiation treatment diagnoses need to be exacting and specific at each radiation target location. Typically important is protection of tissue that is not diseased. Pre-treatment diagnoses also are important for developing a plan for dose rate and duration specifics, for example.

In terms of protecting non-diseased tissue, an example is presented relating to intrauterine diagnosis and treatment where it typically is important to minimize, if not eliminate, radiation exposure to the bladder and the rectum. Generally, marking and diagnosis devices, as well as brachytherapy devices, are visible (or can be rendered visible) under x-ray images or other imaging technologies in order to insure intended placement and to allow the medical physicist or radiation oncology professional to generate a radiation treatment plan specific for this placement and for the particular anatomy and disease location and severity for the particular patient and for each particular treatment event.

It will be appreciated that radiation delivery systems can be used in treatments that are applied manually or remotely using remote afterloading systems. In remote afterloading systems, the radioactive materials are delivered from a safely contained access location to distal reaches of the delivery tubes at treatment portions or locations. Radioactive material can be in the form of wires, seeds, liquids or other species. In such systems, the radioactive material typically is delivered via remote control, such as by operation of a motor, after the medical professionals are out of view from the treatment room. Such remote delivery equipment can move the radioactive dose into the applicator already positioned within the body cavity, the accuracy of which is facilitated by the marking and diagnosis device or catheter.

SUMMARY

There are several aspects of the present subject matter that may be embodied separately or together in the systems, devices and methods described herein and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, systems, devices and methods provide a significantly improved diagnostic tool and procedure before, during and/or after radiation therapy in or near body cavities accessible through existing orifices or percutaneously when desired.

In another aspect, improvements in systems, devices and methods provide the medical professional with a view of the body cavity or target percutaneous location while imaging, such as radiographic viewing or CT scanning, and if desired during radiation treatment itself.

In another aspect, the medical professional diagnostician or treatment physician applies or utilizes the system, device or method to move, push or otherwise manipulate body tissue for the purpose of improved diagnosis or marking and during radiation therapy.

Another aspect is to enable introduction of radiographic fluids or air into the body cavity or other treatment site of the patient without subjecting the patient to risk of direct contact with radiographic and/or radiopaque fluids, while providing real-time detection of and reporting upon treatment specifics.

In another aspect, the system, device and method maintain a desired positioning of the diagnostic balloon having detecting capabilities through the use of securement components such as balloons, clips, templates, tethers or the like while detecting and/or formulating specifics for treatment.

In a further aspect, the system, device and method are especially suitable for use in conjunction with the bladder or other body locations by providing an elongated insertion catheter having drainage characteristics in combination with detection capabilities.

Yet another aspect of the system, device and method includes providing radiopaque reference lines, or reference designations otherwise visible to the attending medical professional, at desired locations within the body. Some can be tailored for one or more of a variety of body cavities and along portions of the device that can be viewed on components of the device that are external of the body when inserted during diagnosis, mapping, marking or treatment, in order to facilitate re-positioning of detectors and balloons for a future insertion in that same patient. Same can include scale markings along a proximal portion of the catheter body.

In an added aspect, the physician is provided with equipment and techniques for diagnosing, mapping and marking in preparation for treatment of any of a wide variety of cancers such as those inside or in the proximity of body cavities including the bladder, vagina, rectum, subglottic, superglottic or glottic regions, stomach, bronchial tubes, nasopharynx or larynx regions, eye sockets, and other intracavity areas. Interstitial insertion of devices through tissue and percutaneous procedures also are encompassed, such as the treatments of the breast, central nervous system, prostate, lung lesions and liver lesions, insertion being through a surgically made opening or percutaneous entry. Treatment can proceed while the diagnostic, mapping and marking device is within the body and later retrieved or removed and subsequently reinserted depending upon the treatment protocol being followed. Catheter-type channels can be used for delivery of radioactive solutions, such as to the balloon. Also, microdiodes can be incorporated to achieve real-time treatment capabilities, and hyperthermia components can be included for enhancing diagnosis and effect of subsequent treatment.

In a further aspect, a system, device and method includes at least one intracavitary balloon component that is sized, shaped, positioned and adapted to impart a space separation between the radiation source emanating (or to be emanating) from the device and an internal location within the body at which radiation treatment is not desired. Each balloon can be a separate unit provided in association with or secured to the device. In other approaches, one or more balloons are secured to a component of the device, which can be used for delivery of radioactive material, solutions or the like. Catheter-type channels can be used for delivery of radioactive solutions, such as to the balloon. Typically microdiodes are incorporated to achieve real-time reporting and marking capabilities during mapping, marking, analyses and radiation treatment, and hyperthermia components can be included.

Another aspect facilitates long-term, low dose rate radiation by enabling introduction of nutrients, fluids, air or other gasses and/or enabling evacuation of wastes and/or gasses through a diagnostic device itself. Catheter-type channels can be used for the delivery of marking solutions, such as through the balloon, microdiodes being incorporated to achieve real-time treatment capabilities, and hyperthermia components can be included.

Another aspect provides a system, device and method suitable for use in marking, mapping and diagnosing bladder carcinoma by providing an elongated insertion catheter having drainage characteristics. Catheter-type channels can be used for delivery of radioactive solutions, such as through the balloon, microdiodes are incorporated to achieve real-time treatment tracking, and hyperthermia components can be included.

Another aspect permits the physician to tailor the size, placement and duration of radiation treatment specifics to the particular therapeutic requirements of the diseased tissue to be treated. Catheter-type channels can be used for positioning of radiopaque material or solutions, such as to the balloon, microdiodes are incorporated to achieve real-time treatment assessment, and hyperthermia components can be included.

Another aspect maintains the positioning of diagnostic devices including balloons through the use of a relatively small or secondary balloon located within a larger therapeutic balloon. Catheter-type channels can be used for delivery of radiopaque solutions, such as to the large balloon, microdiodes are incorporated to achieve real-time treatment assessment, and hyperthermia components can be included.

An additional embodiment concerns a system, device and method for diagnosing, mapping and marking in advance of and/or during radiation therapy wherein a radiation detector and a radiation data receiver are included to provide real-time feedback, including during treatment, or after-treatment recording of treatment specifics. In a particular embodiment, at least one radiation detector is positioned on or in a balloon component, which balloon component is sized, shaped, adapted and positioned to provide positioning, visible by way of appropriate imaging, and confirmation of separation and/or positioning with respect to the radiation source during treatment.

Yet a further embodiment concerns a system, device and method for diagnosis, mapping or marking in conjunction with brachytherapy that includes, in combination, a hyperthermia sub-system and at least one radiation detector, both positioned in the close vicinity of the radiation delivery location or anticipated radiation delivery location along the catheter-like component. A radiation data receiver is located external of the body within which the brachytherapy is expected or is proceeding. Alternatively, the detector may be fixed and its data later able to be analyzed.

BRIEF DESCRIPTION OF THE DRAWINGS

FIG. 4 is a somewhat schematic view, partially in cross-section, of a further embodiment for use within the bladder; and FIG. 5 is a cross-sectional view along the line 5-5 of FIG. 4.

DESCRIPTION OF THE ILLUSTRATED EMBODIMENTS

Figure 1:
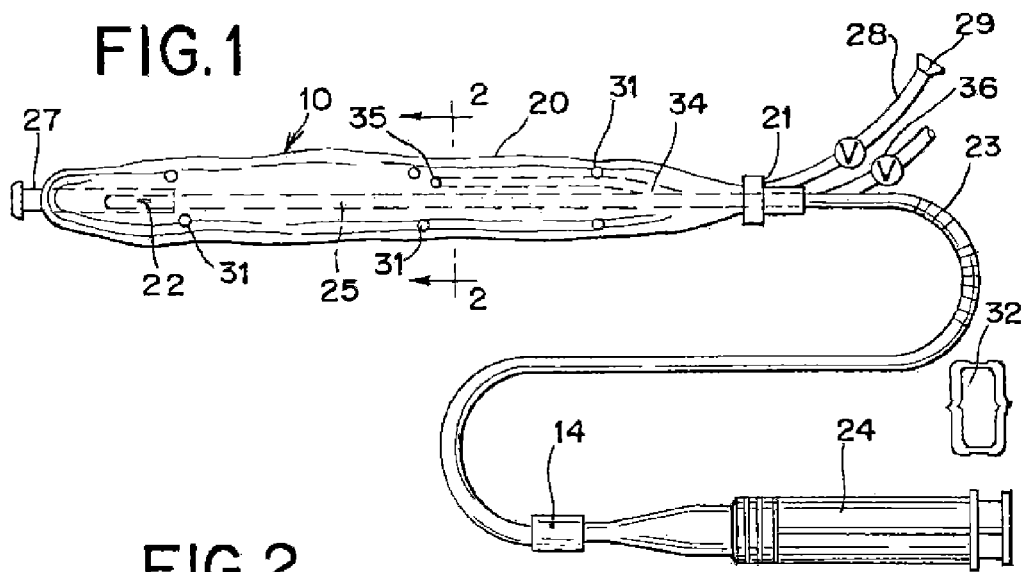
FIG. 1 is an elevation view of an embodiment including a balloon that is inflatable and deflatable along a distal portion of a catheter.

The embodiments disclosed herein are exemplary only, and the subject matter described herein can be embodied in various forms. Therefore, specific details described herein are not to be interpreted as limiting the subject matter as defined in the accompanying claims.

Certain of the illustrated embodiments utilize a catheter for insertion into a body cavity. A balloon is secured to a tubular catheter body, the balloon being positioned and sized for insertion into a particular type of body cavity to be treated. The proximal end of the catheter has one or a plurality of passageways to enable fluid communication through one or more channels in the catheter body, depending upon the embodiment. Such passageway typically utilizes one-way or two-way valves, regulators, hypodermic syringes or other devices for introduction, control and/or withdrawal of fluids into and out of one or more balloons and/or body cavities. The fluid for manipulating the balloon in certain embodiments may be filled with a biocompatible gas, such as air, or a biocompatible liquid, such as saline solution, or with a radiopaque fluid to facilitate viewing. In some embodiments, the fluid can itself have a treatment function. The catheter balloon is sized, shaped and adapted in order to move, expand or otherwise manipulate the body component to be treated or to be positioned in order to prevent or minimize treatment, all with the objective of providing more effective and safer radiation treatment.

One or more detectors and/or hyperthermia components typically are associated with the balloon, which association can modify the positioning of such detector or hyperthermia component being controlled external of the subject's body within which the device is inserted. For example, the balloon can contain receiving members to hold the detector and/or hyperthermia component within the balloon material, or strips of elastomeric or adhesive material along the inside surface or along the outside surface of the balloon can be provided. Other holding approaches can be followed such as placement within a balloon wall thickness, on or in the catheter tube or by way of bowing or free-floating arms or spokes.

For example, the detector or hyperthermia components can be elongated treatment members, or treatment components positioned on elongated members, typically inside of the balloon, and that are secured at one or both of their respective end portions. When desired, same can generally follow end portions of the balloon. In such approaches, the elongated members bow out when within the balloon as the balloon is inflated or expanded. Or the elongated members may be positioned immediately inside the neck of the balloon where attached to the catheter and are otherwise freely suspended within the balloon, not necessarily secured to the balloon at both proximal and distal portions. Even in that event, the elongated treatment members can be secured together at their respective distal end portions to facilitate bowing out of the elongated members. Alternatively, one or both end portions of the elongated members can be located within the polymeric material of the balloon or of the catheter, or between material layers of the balloon or catheter, in order to provide a gathering function for the portions of the elongated members at an attachment location.

Different embodiments can utilize one or more of a variety of approaches to secure the catheter device during the marking, mapping, diagnosing or positioning function or functions and also during subsequent radiation therapy. These securement embodiments and approaches include, for example, a secondary inner balloon, a secondary distal balloon, a template, a catheter lead, and one or more secondary outer balloons, with or separate from tether catheters.

When provided, a secondary inner balloon, which usually is substantially smaller than the main balloon, assists in holding the catheter device in place within the body cavity or location of interest, typically located generally within and at the proximal end portion of the main balloon. Upon inflation or expansion, the secondary balloon secures the catheter device within the body cavity or location of interest by restricting movement of the device at the body orifice or surgical opening. A secondary outer balloon, if and when included, is located distal of the main balloon. When inflated or expanded, same anchors the catheter device at a location downstream or distal of the main balloon.

Some embodiments lend themselves to include a template to secure the catheter device at a location external of the body, such as a body cavity orifice or in areas surrounding a surgical opening. Such a template may be secured by one or combinations of approaches. The template can be sutured to tissue in the vicinity of the body insertion location, or same can be adhered to tissue in the vicinity of the body insertion location, for example, using adhesive or glue. The template can be secured by attaching secondary catheters secured in orifices near the body insertion location. Securement may also be provided by a distally extending catheter lead which anchors the catheter device by slipping the distal end lead through a narrow section of the body, such as at the cervix or duodenum when a body cavity is treated. Devices of this type assist in avoiding unintended movement of the catheter device during marking and diagnosis and during treatment following the marking or diagnosis.

Some embodiments can incorporate a drainage catheter function, such as in conjunction with radiation therapy in the bladder. When provided, such a drainage catheter enables liquids or gasses, including those produced by the body before and while the catheter device is inserted in the body. This eliminates or reduces potentially disruptive distortions caused by gas or liquid build-up and/or dissipation that can change balloon, detector and hyperthermia component placement during marking, diagnosis and treatment.

One or more detectors, such as a diode or a microdiode, facilitate treatment and evaluation of the radiation therapy regimen, typically in association with a hyperthermia treatment. Each detector senses and, if desired, leads to recordal of dose amounts and an indication of location for marking, mapping, diagnosis or detection. Detectors can be embedded in another component such as a balloon or a catheter, or they can be positioned on or in such component. In many instances, it is advantageous to provide detectors in a symmetrical array, for example, evenly spaced from each other or from a reference location. Detectors also can be movable and/or removable. Positioning can be anterior, posterior, right plane or left plane, for example.

Further details concerning devices and approaches noted herein, including device securement, balloon size adjustment, detectors, hyperthermia, for example, are noted in copending U.S. application Ser. No. 13/786,640, filed Mar. 6, 2013, and U.S. Pat. No. 5,520,646, U.S. Pat. No. 5,653,683 and U.S. Pat. No. 5,720,717, which are hereby incorporated by reference hereinto. Certain specific embodiments now are described.

FIG. 1 shows a diagnostic catheter, generally designated at 10, having a body or tube member or catheter 23. A balloon or diagnostic balloon 20 is secured to the catheter 23, being positioned over and sealed onto a distal end length or portion of the body member or catheter 23. This distal end length and the balloon 20 are intended to be inserted by the medical professional or physician into the body of the patient during a diagnostic procedure that can include marking and/or mapping and/or reporting during treatment for immediate and/or post-treatment analysis.

Balloon 20 typically is made of a polymer that has elastomeric properties, although for some uses, the polymeric balloon need not be elastomeric but only need be expandable from a collapsed condition to an expanded condition, such as would be the case for a balloon of polyethelene terephthalate, for example. The catheter body 23 typically is made of a polymeric material, a metallic material, or a combination of polymeric material with metallic material, such as strands of metal embedded in a polymer in order to create the desired balance of flexibility and rigidity.

It is possible for the length and profile of the balloon (or multiple balloons when provided) to be adjustable by means of an adjustment member or assembly 21. Illustrated in this regard in this embodiment is a slidable clip. Although the balloon usually will already be sealed to the catheter body member 23 at its proximal end, as well as at its distal end in most embodiments, the adjustment member 21 allows the physician or other medical professional to select a location for the proximal end of the balloon. For example, when the adjustment member is a slidable clip, same can be of a type that is a cuff that of variable in circumference, the circumference being increased to facilitate movement of the slidable clip either distally or proximally in order to, in effect, adjust the length of the balloon 20, after which the cuff circumference is reduced and locked in place. When a desired balloon length is thus provided, the reduced and locked circumference provides a temporary seal between the balloon and the catheter at the location of the slidable clip, at which time the slidable clip is locked into place by any suitable mechanism. In this manner, the balloon will inflate in the proximal direction only up until the location of this adjustment member 21.

At its proximal end, catheter body 23 may juncture into a plurality of branches. Each branch contains a separate, isolated passageway which communicates through the catheter and to an appropriate component. For example, one such passageway includes a fitting 14 that connects with a pressurized fluid source, which may be a biocompatible gas or liquid, which may or may not be radiopaque to enhance image visibility. As an example, a means of pressurization is provided that is a hypodermic syringe 24. This passageway proceeds the length of the catheter body 23, including its length 25 internal of the balloon 20 within which one or more fluid orifices 22 are provided. This forms a passageway between each orifice 22 and the pressurized fluid source 24. The balloon 20 is inflated or deflated (or reduced in inflation) to vary the balloon size in accordance with the needs of a particular case. For example, it often is desirable in this embodiment to have the balloon engage or become as close as possible to the diseased tissue. This action also can be used to modify the location of the detector or detectors (discussed elsewhere herein) with respect to either diseased tissue to be targeted for treatment, or tissue that is not intended to be directly radiation treated. This action also can be used to adjust spacing between a detector and a radiation source and/or between a radiation source and the tissue to be treated and/or between a detector and the tissue to be treated and/or to vary the placement of fluid inside the catheter such as radiopaque material or low-grade radiation treatment, or radiation shielding.

The embodiment of FIG. 1 includes a further passageway 26, same functioning primarily as a drain or dissipater of fluids, such as urine or other liquids, or gasses found in or developed in the body cavity being treated or in the vicinity of the treatment location. Passageway 26 runs from within an input tube 27, continuing through a proximal tube 28, which can terminate at a connector 29, such as a luer-lock allowing connection to a suitable collector, such as a urine bag (not shown in this embodiment).

The diagnosis balloon 20 may be shaped so as to be generally round, oblong, semi-circular or curved along one side and flat along another side, such as being generally D-shaped in cross-section. Different balloon cross-sectional shapes can tailor the device for specific radiation treatment sites.

A plurality of detectors 31 are positioned inside the balloon 20 in this embodiment. Detectors in this regard are diodes, microdiodes, mini-dosimeters or other data collecting devices that can be used to transmit data for "real-time" measurement, mapping, marking, observation and/or recordal of such data. For example, when the device is implanted or inserted for marking, mapping or diagnosis purposes, the detectors provide information on any radiation existing at that time, such as residue from a previous treatment, both in terms of location and magnitude. When the diagnostic catheter 10 is in place during radiation treatment, the detectors 31 will observe and transmit location and magnitude information on treatment radiation. Treatment radiation can be of various types. For example, same can be external beam radiation and/or can be brachytherapy radiation on a body member or cavity that is different from the one within which the diagnostic catheter 10 is inserted, thereby monitoring for any possible radiation spillover. In addition, the diagnostic catheter 10 can be implanted or inserted into the body cavity or percutaneous location that is undergoing or soon to undergo brachytherapy or external beam radiation, or the diagnostic catheter 10 can be at a location immediately adjacent to the brachytherapy procedure or external beam target.

It will be appreciated that the detector or detectors will communicate with appropriate data receptors, which communication can be wireless or can enlist the use of a transmission wire or lead (not shown). A wireless data receptor 32 is shown in FIG. 1. Data received thereat is processed, displayed and/or stored in accordance with practices known in the art.

Figure 2:
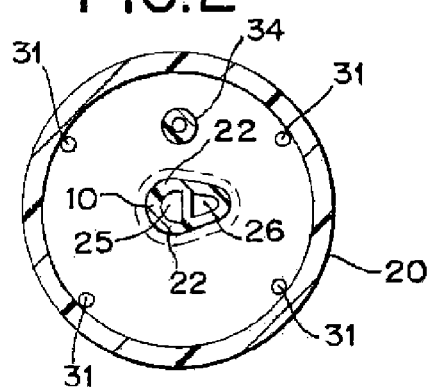
FIG. 2 is a cross-sectional view along the line 2-2 of FIG. 1.

FIG. 1 also incorporates a hyperthermia system by which heat can be applied within the balloon and thus to the detectors 31 and/or to surrounding tissue, whether during marking, mapping, diagnosis and/or treatment. The illustrated hyperthermia system includes a delivery tube 34 having a distal end portion outlet 35 and continues external of the diagnostic balloon 20 and catheter 23, which passageway can be selectively opened and closed by a valve 36. Details of the placement of the hyperthermia delivery tube 34 and other components of this embodiment are seen in FIG. 2. Multiple hyperthermia tubes can be provided. When desired, the hyperthermia tube or tubes can be used for or in association with low dose rate (LDR) or high dose rate (HDR)/radiation treatment from whatever source is associated with the diagnostic catheter. For example, same can be based on microwave, ultrasound and/or radiant energy, or some other type of method. Hyperthermia application in this manner is for enhancing the effect of diagnoses and improving radiation treatment effectiveness that can be observed via the detector system.

Figure 3:
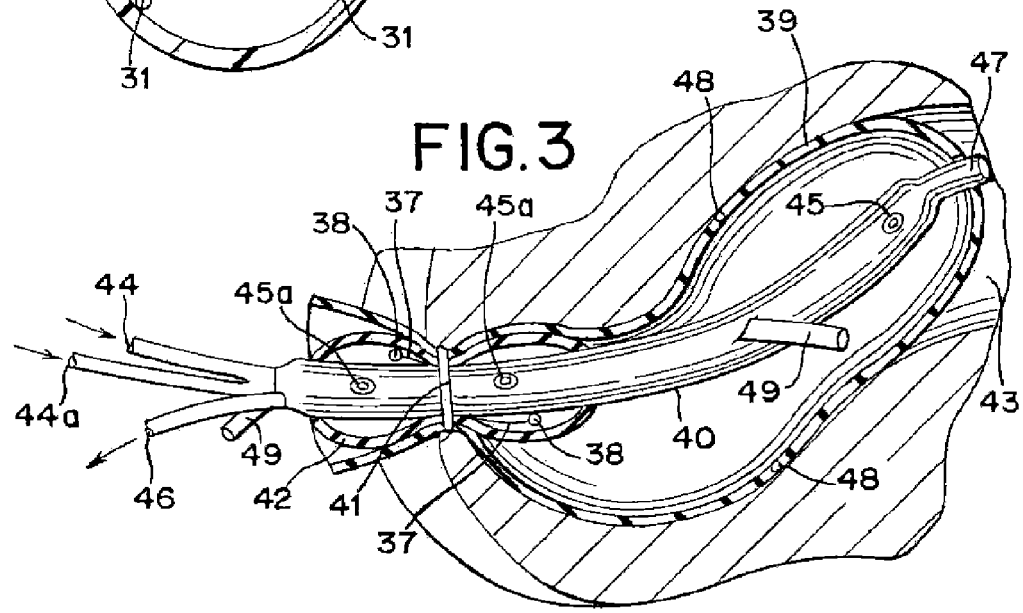
FIG. 3 is a somewhat schematic view, partially in cross-section, of a further embodiment for use within the rectum.

FIG. 3 illustrates a diagnostic catheter with a catheter tube or body 40 that incorporates a secondary or positioning balloon 42, which is considerably smaller than the primary or diagnostic balloon 39 of this embodiment, as well as an adjustment member 41 functioning in the manner of member 21. The distal portion of this diagnostic catheter is inserted into the patient's rectal cavity 43 in this embodiment. The adjustment member, e.g., slidable clip 41, and secondary balloon 42 are positioned so as to be located at the orifice of the patient, with the portion of the balloon distal of the adjustment member 41 being within the rectal cavity in this illustration. To facilitate location, the adjustment member 41 can be radiopaque for marking purposes.

Proximal and distal ends of the positioning balloon 42 are adhered to the catheter body 40, and the adjustment member 41 may be secured anywhere along the length of the positioning balloon 42. Separate respective inflation passageways 44, 44a are illustrated for controlling the inflation of the respective balloons through respective catheter holes 45, 45a. If desired, the two holes 45a could themselves be separately filled by another inflation passageway 44a or by bifurcating such passageway. Drainage of bodily fluids, liquids and/or gasses can be achieved by provision of passageway 46 having input tube 47.

A plurality of detectors 48 are positioned within the walls of the primary balloon 39, each being provided for transmission of radiation data to a receptor (not shown). In addition, a hyperthermia delivery tube 49 opens into the primary balloon 39. Detectors 48 and hyperthermia components including tube 49 are functional in the manner generally discussed hereinabove with respect to the embodiment of FIG. 1 and FIG. 2. In addition, supplemental detectors 38 are shown positioned within the secondary or positioning balloon 42, either secured to the balloon or to the catheter tube 40. Alternatively, the detectors can be relatively free-floating, being secured by way of a tether 37. When associated with the positioning balloon 42, the detector 38 can be on the inside surface of the balloon, on the outside surface of the balloon, or embedded within the wall of the balloon 42. However secured in place, the supplemental detector 38 indicates radiation in the vicinity of the positioning balloon 42 and can indicate differences in radiation immediately within and immediately without of the body cavity undergoing diagnosis.

The volume between the inflated diagnostic balloon 39 and the diagnostic catheter tube 40 can be filled with material that does more than inflate or deflate the balloon. For example, same can be filled with contrast liquid or fluid, with water, with saline solution, with a liquid radioisotope when low-grade radiation treatment is desired, or combinations thereof.

FIG. 4 illustrates a catheter, generally designated at 50, for diagnosis in a bladder 51. The particular illustrated bladder is a male bladder; however, this embodiment is suitable for use in female bladders as well. This diagnostic catheter includes a catheter tube or body 52 having a drainage passageway tube 53 through which fluid, liquid or gas can escape after entering at input tube 54. A detachable urine bag 55 is shown. This diagnostic catheter includes a diagnostic balloon 56 secured to the catheter tube 52. A radiopaque reference line 57 is provided on the balloon in this embodiment.

The diagnostic catheter 50 of FIG. 4 and FIG. 5 is inserted through the urinary tract 58 into the bladder 51. Catheter tube 52 exhibits a plurality of passageways. Passageway 59 continues into branch 61 having the drainage catheter tube 53. Passageway 62 continues into branch 63 through which the inflation and deflation of the balloon 56 proceeds.

Diagnostic balloon 56 is inflated by way of one or more holes 64, and the balloon is secured to the catheter at proximal neck 65 and distal neck 65a. A plurality of detectors 66 are positioned in an array along a plurality of spokes 67. In this embodiment, all of the detectors and spokes are within the balloon.

In this illustrated embodiment, the distal end portions of the spokes 67 join a slidable hub 68 at a location along the catheter 52. A manipulation wire 69 is joined at its distal end to the hub 68. Manipulation wire 69 continues proximally through the catheter tube 52 and to branch 70 thereof, this branch having a passageway 71 that slidingly receives the manipulation wire 69. Inserting the manipulation wire 69 further into the passageway 71 moves the hub 68 distally, thereby reducing the bowing of the spokes 67 and thereby moving the detectors 66 generally radially inwardly. Moving the manipulation wire 69 outwardly pulls the hub 68 in a proximal direction, thereby increasing the bowing of the spokes 67 and moving the detectors generally radially outwardly. This action allows the medical professional to modify the detector array from an external position, thereby varying detector positioning in order to probe for changes or in order to modify radiation location and magnitude without having to remove the diagnostic catheter 50 from the body cavity.

While FIG. 4 shows use of this diagnostic catheter 50 within the bladder, same can be suitable for use elsewhere as well, which may or may not involve a modification in the shape of the catheter and of the balloon. For example, some embodiments can have a more elongated balloon for body passageways that are not as symmetrical as that illustrated in FIG. 4. Also, hyperthermia components can be included in such an embodiment as generally disclosed herein with respect to other embodiments. Although the spokes are shown in FIG. 4 to be generally uniformly positioned and spaced, variations can be provided in order to better conform to body cavity shapes for an expected use of the device. For example, the spokes can have separate sliding lengths, and modification of the bowing of the spokes can be independently generated by providing a plurality of manipulation components, for example one for each spoke.

As a general proposition, chemotherapy materials can be included in conjunction with one or more of the radiation treatment devices described herein. Such delivery can be, for example, practiced by way of delivery tubes such as those shown herein for a hyperthermia function in those instances where separate tubing is desired for chemotherapy delivery. Additionally or alternatively, one or more of the balloons or catheter in some embodiments, can have impregnated into, infused onto, coated on, or otherwise carry chemotherapy materials separate and apart from being able to be delivered from the outside after insertion into the body. Chemicals or drugs along these lines can be provided in the form of microspheres or other organically bound or chemically bound substances as alternative chemotherapy or radioactive delivery systems. For example, delivery of Bacillum calmette-guerin (BCG) for bladder cancer treatment can be used. In other embodiments, the substance delivered by any of these means can be useful for pain maintenance, such as analgesic materials and pain or narcotic materials to provide pain relief during procedures, especially when the device protocol requires insertion within the body for extended time periods. These can include delayed release analgesics and the like.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A catheter, comprising:
    a catheter body that is sized, shaped and adapted to not deform under pressure encountered during passage from an insertion location to a target location within a subject of radiation treatment at the target location, the catheter body having a distal end portion and an outside surface;
    a balloon affixed to the catheter body, the balloon having a proximal end portion secured to the catheter body at a location proximal of the distal end portion of the catheter body, a distal end portion secured to the distal end portion of the catheter body, an inner surface and an outer surface and a wall thickness between the surfaces;
    at least one detector that collects data on radiation, the detector being movable with respect to the balloon, the balloon having sufficient axial strength and radial extendability to cooperate in adjusting positioning of the detector with respect to the target location;

at least one spoke secured at two spaced-apart locations, a first of the spaced-apart locations being at which the spoke is secured to the catheter body at a location proximal of the distal end portion of the catheter body and distal to the proximal end portion of the balloon, a second of the spaced-apart locations being joined to a hub slidable along the catheter body between the distal end portion of the balloon and the first spaced-apart location, the spoke is structured whereby the spoke bows to varying degrees in response to changing the distance between the two spaced-apart locations, wherein the detector is attached to the spoke, and wherein the changing the distance between the two spaced-apart locations also changes the location of the detector with respect to the catheter body and the balloon;

the balloon is located radially outward of the spoke;

a hyperthermia component that delivers hyperthermia treatment to the balloon; and the data collected by the detector monitors radiation recognized by the detector at the target location, which data is collected for further processing.

2. The catheter in accordance with claim 1, further including radiopaque reference marking associated with the balloon, the radiopaque reference marking being selected from the group consisting of biocompatible fluids within the balloon, radiopaque fluids within the balloon, one or more radiopaque markings on the diagnostic balloon, and combinations thereof.

3. The catheter in accordance with claim 1, further including an adjustment member that engages the proximal end portion of the balloon, the adjustment member being movable to increase or decrease the inflatable internal volume of the balloon.

4. The catheter in accordance with claim 1, wherein the balloon provides manipulation of the target location within the subject by expansive engagement between the balloon and the target location upon inflation of the balloon.

5. The catheter in accordance with claim 1, comprising a plurality of the spokes spaced apart generally circumferentially.

6. A catheter, comprising:

a catheter body that is sized, shaped and adapted to not deform under pressure encountered during passage from an insertion location to a target location within a subject's body, the catheter body having an outside surface, a proximal end portion and a distal end portion;

a balloon secured at the distal portion of the catheter body, the balloon having a collapsed condition and an expanded condition, the balloon including at least one imaging visibility member;

a plurality of detectors, each detector collects data on radiation;

a plurality of spokes each secured at two spaced-apart locations, a first of the spaced-apart locations being at which each spoke is secured to the catheter body at a location proximal of the distal end portion of the catheter body and distal to the proximal end portion of the balloon, a second of the spaced-apart locations being joined to a hub slidable along the catheter body between the distal end portion of the balloon and the fist spaced-apart location, the each spoke is structured whereby the spoke bows to varying degrees in response to changing the distance between the two spaced-apart locations, the spokes being spaced apart generally circumferentially, each spoke having at least one of said detectors attached to the spoke, wherein the changing the distance between the two spaced-apart locations also changes the location of the detector of that spoke with respect to the catheter body and the balloon, and the detectors are provided as an array of detectors on one or multiple spokes;

the balloon is located radially outward of the spokes;

the catheter body has a longitudinal passageway that extends from outside the target location to the distal portion of the catheter body while within the subject's body;

a marking source selected from the group consisting of a biocompatible fluid within the balloon, a radiopaque fluid within the balloon, a radiopaque mark on the catheter, and combinations thereof; and the data collected by the detectors monitor radiation recognized by each detector from a medical radiation source.

7. The catheter in accordance with claim 6, further including a securement member affixed to the catheter, the securement member secures the catheter to the subject's body, and a detector is associated with the securement member.

8. The catheter in accordance with claim 6, wherein the balloon is substantially longer than wide, and is sized, shaped and adapted such that when inflated, the balloon engages internal tissue of a region of the target location, said passageway permitting external flow of body liquids or gasses or internal flow of nutrients, chemicals, drugs, chemotherapy systems, radioactive delivery systems, pain maintenance materials, narcotic materials, or combinations thereof through the passageway while the catheter is within the subject's body.

9. The catheter in accordance with claim 6, wherein the catheter body includes scale markings along a proximal portion thereof.

10. The catheter in accordance with claim 6, wherein chemicals, drugs, chemotherapy, analgesic material, or a combination thereof is delivered by a tube that is impregnated, infused, coated or encased by the balloon, the material being fluid, microspheres, organically bound, chemically bound, or combinations thereof.

11. The catheter in accordance with claim 6, further including a hyperthermia component, the hyperthermia component being of the energy type selected from the group consisting of thermal, microwave, ultrasonic and radiant, and combinations thereof, which energy is applied with or without radiation, and whether simultaneously, pre-irradiation or post-irradiation.

12. The catheter in accordance with claim 6, wherein the longitudinal passageway permits external flow of body liquids or gasses or internal flow of nutrients, chemicals, drugs, chemotherapy systems, radioactive delivery systems, pain maintenance materials, narcotic materials, or combinations thereof through the passageway while the catheter is within the subject's body.

13. A procedure for therapeutic radiation treatment, comprising:

selecting a catheter including a catheter body having a distal end portion, a balloon with a proximal end portion secured to a catheter body location proximal of the distal end portion of the catheter body, the balloon having a distal end portion secured to the distal end portion of the catheter body, a passageway which permits passage of inflation fluid into and out from the balloon, a plurality of detectors movably mounted with respect to the catheter body, balloon or both, a plurality of spokes each secured at two spaced-apart locations at which the spoke is secured to the catheter body, a first of the spaced-apart locations being at a location proximal of the distal end portion of the catheter body and distal to the proximal end portion of the balloon, a second of the spaced-apart locations being joined to a hub slidable along the catheter body between the distal end portion of the balloon and the fist spaced-apart location, each spoke is structured whereby the spoke bows to varying degrees in response to changing the distance between the two spaced-apart locations, the spokes being spaced apart generally circumferentially, each spoke having at least one of said detectors attached to the spoke, and a marking component viewable through radiopaque viewing equipment outside of an insertion location of a living patient, the balloon being located radially outward of the spokes;

inserting the catheter through the insertion location until a desired length of the balloon is inserted into the insertion location of the living patient to provide a desired catheter penetration depth to a target location;

inflating the balloon thus inserted until the balloon engages internal tissue of the insertion location, thereby moving the marking material or component to thereby assess positioning for radiation treatment, and thereby manipulating the internal tissue of the insertion location by engagement between the balloon and the insertion location;

changing the distance between the two spaced-apart locations to thereby bow the spokes and change the location of the detector or detectors on that spoke with respect to the catheter body and balloon; and collecting data from the detectors, the data including radiation level and location.

14. The procedure in accordance with claim 13, further including passing fluids between the insertion location and a location exterior of the catheter, the passing being through the catheter body.

15. The procedure in accordance with claim 13, further including delivering companion treatment regimens selected from the group consisting of chemicals, drugs, radioactive delivery systems, chemotherapy fluids, chemotherapy microspheres, analgesic fluids, analgesic microspheres, hyperthermia, and combinations thereof.

16. The procedure in accordance with claim 13, further including delivering hyperthermia treatment to the insertion location.

* * * * *